(12) United States Patent
Hautvast

(10) Patent No.: US 8,907,952 B2
(45) Date of Patent: Dec. 9, 2014

(54) REPARAMETRIZED BULL'S EYE PLOTS

(75) Inventor: Guillaume Leopold Theodorus Frederik Hautvast, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 464 days.

(21) Appl. No.: 13/131,094

(22) PCT Filed: Nov. 27, 2009

(86) PCT No.: PCT/IB2009/055387
§ 371 (c)(1),
(2), (4) Date: May 25, 2011

(87) PCT Pub. No.: WO2010/064180
PCT Pub. Date: Jun. 10, 2010

(65) Prior Publication Data
US 2011/0249005 A1    Oct. 13, 2011

(30) Foreign Application Priority Data
Dec. 3, 2008    (EP) .................................... 08170544

(51) Int. Cl.
*G06T 11/20*    (2006.01)
*G06T 17/00*    (2006.01)
(Continued)

(52) U.S. Cl.
CPC ............... *A61B 5/055* (2013.01); *A61B 5/7425* (2013.01); *A61B 5/7435* (2013.01);
(Continued)

(58) Field of Classification Search
USPC ........... 345/440, 424; 715/769; 600/425, 523, 600/476; 382/128, 131
See application file for complete search history.

(56) References Cited

U.S. PATENT DOCUMENTS

| 2005/0008209 A1 | 1/2005 | Matsumoto |
| 2006/0182341 A1 | 8/2006 | Rinck et al. |

(Continued)

FOREIGN PATENT DOCUMENTS

| DE | 10331098 A1 | 2/2005 |
| DE | 102006026695 A1 | 12/2007 |

(Continued)

OTHER PUBLICATIONS

Mark F. Smith et al: "Regional Cardiac Wall Motion From Gated Myocaridal Perfusion Spect Studies"; IEEE Transactions on Nuclear Science, Vol. 46, No. 3, Jun. 1999, pp. 727-736.

(Continued)

*Primary Examiner* — Chante Harrison

(57) ABSTRACT

The invention relates to a system for visualizing, in a first bull's eye plot, results of a first quantitative analysis of an object represented in first image data, in particular for cardiac analysis. The first image data comprises a first plurality of data slices, and the system comprises a slice unit for associating a data slice of the first plurality of data slices with a concentric ring of the first bull's eye plot, a radius unit for computing the length of a radius of the concentric ring of the first bull's eye plot, and a value unit for computing at least one value for displaying in the concentric ring of the first bull's eye plot, on the basis of the data slice associated with the concentric ring of the first bull's eye plot, and wherein the length of the radius of the concentric ring of the first bull's eye plot is defined on the basis of the position of the data slice, of the first plurality of data slices, associated with the concentric ring of the first bull's eye plot, with respect to the object. The dependence of the first bull's eye plot concentric ring radius on the position of the data slice associated with said concentric ring of the first bull's eye plot, with respect to the object, defines an objective framework for the first bull's eye plot, based on the geometry of the object. Thus, the results of the first quantitative analysis of the object visualized in the first bull's eye plot can be more easily compared with results of a second quantitative analysis of the same object represented in second image data visualized in a second bull's eye plot, when the length of the radiuses of the concentric rings of the second bull's eye plot are also defined on the basis of the positions of the data slices associated with said concentric rings of a second first bull's eye plot, with respect to the object. In an embodiment, the corresponding locations in each bull's eye plot may be indicated by couples pointers. In addition, further pointers, each pointer coupled to the respective pointer in one of the bull's eye plots, may be adapted for pointing at corresponding locations in the corresponding data slices of the first and second image data.

18 Claims, 8 Drawing Sheets

(51) Int. Cl.
  *G06K 9/00* (2006.01)
  *A61B 5/00* (2006.01)
  *A61B 5/055* (2006.01)
(52) U.S. Cl.
  CPC ............. *A61B 5/2425* (2013.01); *G06T 11/206* (2013.01); *A61B 9/503* (2013.01)
  USPC ........... 345/440; 345/424; 345/441; 382/128; 382/131

(56) References Cited

U.S. PATENT DOCUMENTS

| | | |
|---|---|---|
| 2006/0241412 A1 | 10/2006 | Rinck et al. |
| 2007/0014452 A1 | 1/2007 | Suresh et al. |
| 2010/0160789 A1* | 6/2010 | Dilworth et al. ............. 600/476 |
| 2010/0215225 A1* | 8/2010 | Kadomura et al. ........... 382/128 |
| 2010/0245360 A1* | 9/2010 | Song et al. ................... 382/131 |
| 2011/0075902 A1* | 3/2011 | Song et al. ................... 382/128 |
| 2012/0089016 A1* | 4/2012 | Mizuno ......................... 600/425 |
| 2012/0151399 A1* | 6/2012 | Soerensen et al. ............ 715/769 |
| 2013/0023780 A1* | 1/2013 | Cardinale et al. ............. 600/523 |

FOREIGN PATENT DOCUMENTS

| | | |
|---|---|---|
| JP | 2004141245 | 5/2004 |
| JP | 2009018005 | 1/2009 |
| WO | 2006118100 A1 | 11/2006 |

OTHER PUBLICATIONS

Stephan G. Nekolla et al: "Reproducibility of Polar Map Generation and Assessment of Defect Severity and Extent Assessment in Myocardial Perfusion Imaging Using Positron Emission Tomography"; European Journal of Nuclear Medicine, Vol. 25, No. 9, Sep. 1998, pp. 1313-1321.

Andre Alfons Dobbeleir: "Quantification and Data Optimisation of Heart and Brain Studies in Conventional Nuclear Medicine"; Thesis Submitted to University of Groningen, 2006, 117 Page Document.

Tadanori Fukami et al: "Quantitative Evaluation of Myocardial Function by a Volume-Normalized Map Generated From Relative Blood Flow"; Physics in Medicine and Biology, vol. 52, No. 14, Jul. 2007, pp. 4311-4330.

Manuel D. Cerqueira et al: "Standardized Myocardial Segmentation and Nomenclature for Tomographic Imaging of the Heart"; Circulation 2002, vol. 105, pp. 539-542.

* cited by examiner (a)

(b)

REPARAMETRIZED BULL'S EYE PLOTS

FIELD OF THE INVENTION

The invention relates to the visualization of quantitative analysis results in a bull's eye plot, in particular to the visualization of quantitative cardiac analysis results.

BACKGROUND OF THE INVENTION

Cardiac imaging can be used to determine local myocardial function, perfusion and viability. Nowadays, such images can be obtained using various modalities such as magnetic resonance imaging (MRI), computed tomography (CT), ultrasound (US) and nuclear medicine (PET/SPECT). The images for function, perfusion and viability may be obtained using one modality (MRI) or using hybrid imaging, for instance PET/CT.

After acquisition, the images are analyzed independently, resulting in a number of measurements performed at different positions at the myocardium. The functional images are used to quantify wall motion abnormalities, the perfusion images are used to quantify perfusion deficits and the viability images are used to quantify scarring of the myocardium.

These measurements produce quantitative data that are usually displayed in so-called bull's eye plots, in which measurement values are color coded and projected on a plane perpendicular to the long axis.

Current cardiac analysis software packages generate bull's eye plots in which each ring in the bull's eye plot corresponds to a particular slice in the stack of acquired images. If a comprehensive cardiac exam is performed, bull's eye plots are made based on the (local) measurements derived from each scan. These bull's eye plots are then included in a comprehensive report. Functional measurements that can be displayed in a bull's eye plot are: end diastolic wall thickness, end systolic wall thickness, wall thickening (both absolute and relative), wall motion, time of maximum contraction, maximum wall thickness etc. Perfusion related measurements that can be displayed in a bull's eye plot include time of peak intensity, time of maximum upslope, upslope ratio rest/stress, etc. Viability related measurements that can be displayed in a bull's eye plot are: percentage of viable tissue, thickness of viable tissue, a transmurality index, etc.

Unfortunately, current scanning procedures do not yet allow acquiring functional, perfusion and viability images of the same resolution. Consequently, the acquired image stacks differ with respect to the slice thickness, slice spacing and the number of slices. Therefore, the derived bull's eye plots consist of arbitrarily distributed different numbers of rings, such that it becomes difficult to compare the complementary information comprised in function, perfusion and viability bull's eye plots. This is illustrated in FIG. 1A showing bull's eye plots derived from a comprehensive cardiac MR exam comprising functional image data containing 10-15 contiguous slices of thickness 8 mm (a), from perfusion images of 3 slices of thickness 20 mm and gaps of 10 mm (b), and viability images of 15-20 slices of thickness 6 mm (c). The bull's eye plots in FIG. 1A are scaled such that they are of substantially the same size.

A standardized myocardial segmentation for tomographic imaging of the heart has been proposed by the American Heart Association (AHA). The AHA proposal is described in AHA Scientific Statement: *Standardized Myocardial Segmentation and Nomenclature for Tomographic Imaging of the Heart*, Circulation 2002; 105:539-542 (available online at http://circ.ahajournals.org/cgi/content/short/105/4/539).

FIG. 1B schematically shows left ventricular bull's eye plot sectors (a) and the corresponding myocardial slices and sectors (b) according to the AHA model. AHA recommends dividing the left ventricle into equal thirds perpendicular to the long axis of the heart to generate three slices of the left ventricle: the circular basal slice 1 comprising sectors 1 to 6, the mid-cavity slice 2 comprising sectors 7 to 12, and the apical short axis slice 3 comprising sectors 12 to 16. The last sector, the apex 17, is shown in a vertical long axis slice 4. The slice thickness should be selected on the basis of modality-specific resolution and clinical relevance and should be less than 1 cm. While the AHA segmentation allows comparing different cardiac study quantitative analyses, the proposed visualization often ignores large chunks of data which are not comprised in said three slices.

SUMMARY OF THE INVENTION

It would be advantageous to have a system which improves visualizing results of a quantitative analysis of a structure comprised in first image data in a first bull's eye plot, which first bull's eye plot can easily be compared to a second bull's eye plot visualizing results of a quantitative analysis of the same structure described in second image data.

The invention is defined by the independent claims. Advantageous embodiments are defined in the dependent claims.

Hence, in an aspect, the invention provides a system for visualizing, in a first bull's eye plot, results of a first quantitative analysis of an object represented in first image data, the first image data comprising a first plurality of data slices, the system comprising:

a slice unit for associating a data slice of the first plurality of data slices with a concentric ring of the first bull's eye plot;

a radius unit for computing the length of a radius of the concentric ring of the first bull's eye plot; and a value unit for computing at least one value for displaying in the concentric ring of the first bull's eye plot, on the basis of the data slice associated with the concentric ring of the first bull's eye plot;

and wherein the length of the radius of the concentric ring of the first bull's eye plot is defined on the basis of the position of the data slice, of the first plurality of data slices, associated with the concentric ring of the first bull's eye plot, with respect to the object.

The radius may be, e.g., the external or the internal radius of the ring. The dependence of the first bull's eye plot concentric ring radius on the position of the data slice associated with said concentric ring of the first bull's eye plot, with respect to the object, defines an objective framework for the first bull's eye plot, based on the geometry of the object. Thus, the results of the first quantitative analysis of the object visualized in the first bull's eye plot can be more easily compared with results of a second quantitative analysis of the same object represented in second image data visualized in a second bull's eye plot when the length of the radiuses of the concentric rings of the second bull's eye plot are also defined on the basis of the positions of the data slices associated with said concentric rings of a second first bull's eye plot, with respect to the object. This is because the length of the radius of a concentric ring associated with a slice of the first plurality of data slices, said slice being at a certain position with respect to the object, will be similar to the length of the radius of a concentric ring associated with a slice of the second plurality of data slices, said slice being at a similar position with respect to the object.

In an embodiment of the system, the data slice associated with the concentric ring comprises a data sector, the slice unit further comprises a slice-sector unit for associating the data sector of the data slice with a ring sector of the concentric ring, the value unit comprises a sector-value unit for computing at least one value for displaying in the ring sector of the concentric ring, on the basis of the data sector associated with the ring sector of the concentric ring, and the position of the ring sector with respect to the concentric ring is defined on the basis of the position of the data sector associated with the ring sector, with respect to the object. By choosing smaller sectors, it is possible to increase the resolution of the first bull's eye plot. Because the position of each sector is based on the position of the corresponding data sector with respect to the object, the objective framework for the first bull's eye plot is based on a more detailed geometry of the object.

In an embodiment of the system, the first bull's eye plot comprises a concentric ring gap corresponding to an inter-slice gap. This may be necessary if the first image data is sparse and comprises, for example, gaps between data slices of the first plurality of data slices. The ring gaps correspond to the gaps between data slices.

In an embodiment, the system further comprises an approximation unit for computing at least one value for displaying in the concentric ring gap of the first bull's eye plot on the basis of data slices of the first plurality of data slices associated with concentric rings adjacent to the ring gap. For example, the system can be adapted to interpolate missing data slices of the first image data. The values in the ring gaps can be computed based on the interpolated data slices.

In an embodiment of the system, the at least one value for displaying in the concentric ring gap of the first bull's eye plot is computed on the basis of values for displaying in the concentric rings adjacent to the ring gap, which values are computed on the basis of data slices of the first plurality of data slices, associated with the concentric rings adjacent to the gap. Using, for example, radial (1-dimensional) or polar (2-dimensional) interpolation of the bull's eye plot values, the system may be adapted for computing values for displaying in the ring gap.

In an embodiment of the system, the length of the radius of the concentric ring of the first bull's eye plot is computed on the basis of a distance between the data slice of the first plurality of data slices, associated with the concentric ring, and a certain feature of the object. The distance may be defined as the distance between the upper surface of the slice and a point-feature of the object.

In an embodiment of the system, the width of the concentric ring of the first bull's eye plot is computed on the basis of the thickness of the data slice of the first plurality of data slices.

In an embodiment of the system, the first bull's eye plot is substantially smooth, i.e., there are substantially no ring edges corresponding to slice boundaries visible in the bull's eye plot. This may be achieved, for example, when the first plurality of data slices comprises a large number of thin data slices, or using interpolation.

In an embodiment, the system is further adapted for visualizing, in a second bull's eye plot, results of a second quantitative analysis of second image data, the second image data comprising a second plurality of data slices. In this embodiment:

the slice unit is adapted for associating a data slice of the second plurality of data slices with a concentric ring of the second bull's eye plot;

the radius unit is adapted for computing the length of a radius of the concentric ring of the second bull's eye plot; and the value unit is adapted for computing at least one value for displaying in the concentric ring of the second bull's eye plot on the basis of the data slice associated with the concentric ring of the second bull's eye plot;

and the length of the radius of the concentric ring of the second bull's eye plot is defined on the basis of the position of the data slice, of the second plurality of data slices, associated with the concentric ring of the second bull's eye plot, with respect to the object.

For example, the first and second bull's eye plot showing, respectively, functional and perfusion analysis results may be displayed next to each other for an easy visual inspection by a physician.

In an embodiment of the system, the lengths of the radiuses of the concentric ring of the first bull's eye plot and of the concentric ring of the second bull's eye plot are computed on the basis of distances from, respectively, the data slice of the first plurality of data slices and the data slice of the second plurality of data slices to a certain feature of the object.

In an embodiment, the system further comprises:

an indicator input unit for receiving a user input for indicating a first location in the first bull's eye plot, using a first indicator, and a second location in the second bull's eye plot, using a second indicator; and an indicator unit for indicating the first location in the first bull's eye plot, using the first indicator, and the second location in the second bull's eye plot, using the second indicator, based on the user input;

wherein the first and second locations are substantially the same relative to the respective first and second bull's eye plots.

Thus, the indicated first and second locations correspond to substantially identical locations in the first and second image data. The first and second bull's eye plots are displayed on a display. The indicators help the user compare the results of the first and second quantitative analysis.

In an embodiment, the system further comprises a slice determination unit for determining a first ring comprising the first location, based on a first data slice associated with the first ring and for determining a second ring comprising the second location, based on a second data slice associated with the second ring. Thus, a comparison of the first and second ring is possible. Optionally, the corresponding first and second data slice may be also displayed next to the corresponding bull's eye plots.

In an embodiment of the system, the user input for indicating the first location in the first bull's eye plot comprises a certain location in a certain data slice of the first plurality of data slices. In this embodiment, the user may navigate through the first plurality of data slices. The system is adapted for displaying the slices selected by the user for viewing. The user may view the displayed slices, and select a certain location in a certain slice. This certain location is indicated by the indicator unit in the first bull's eye plot, in the ring associated with the certain slice, using the first indicator.

In a further aspect of the invention, the system is comprised in a reporting system for creating a report.

In a further aspect of the invention, the system is comprised in an image acquisition apparatus.

In a further aspect of the invention, the system is comprised in a workstation.

In a further aspect, the invention provides a method of visualizing, in a first bull's eye plot, results of a first quantitative analysis of an object represented in first image data, the first image data comprising a first plurality of data slices, the method comprising:

a slice step for associating a data slice of the first plurality of data slices with a concentric ring of the first bull's eye plot;

a radius step for computing the length of a radius of the concentric ring of the first bull's eye plot; and a value step for computing at least one value for displaying in the concentric ring of the first bull's eye plot, on the basis of the data slice associated with the concentric ring of the first bull's eye plot;

wherein the length of a radius of the concentric ring of the first bull's eye plot is defined on the basis of the position of the data slice, of the first plurality of data slices, associated with the concentric ring of the first bull's eye plot, with respect to the object.

In a further aspect of the invention, a computer program product to be loaded by a computer arrangement is provided, the computer program product comprising instructions for visualizing, in a first bull's eye plot, results of a first quantitative analysis of an object represented in first image data, the first image data comprising a first plurality of data slices, the computer arrangement comprising a processing unit and a memory, the computer program product, after being loaded, providing said processing unit with the capability to carry out the tasks of:

associating a data slice of the first plurality of data slices with a concentric ring of the first bull's eye plot;

computing the length of a radius of the concentric ring of the first bull's eye plot; and computing at least one value for displaying in the concentric ring of the first bull's eye plot, on the basis of the data slice associated with the concentric ring of the first bull's eye plot;

and wherein the length of a radius of the concentric ring of the first bull's eye plot is defined on the basis of the position of the data slice, of the first plurality of data slices, associated with the concentric ring of the first bull's eye plot, with respect to the object.

It will be appreciated by those skilled in the art that two or more of the above-mentioned embodiments, implementations, and/or aspects of the invention may be combined in any way deemed useful.

Modifications and variations of the reporting system, of the image acquisition apparatus, of the workstation, of the method, and/or of the computer program product, which correspond to the described modifications and variations of the system, can be carried out by a person skilled in the art on the basis of the present description.

A person skilled in the art will appreciate that the method may be applied to multidimensional image data, e.g., to 3-dimensional or 4-dimensional images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will become apparent from and will be elucidated with respect to the implementations and embodiments described hereinafter and with reference to the accompanying drawings, wherein.

Identical reference numerals are used to denote similar parts throughout the Figures.

DETAILED DESCRIPTION OF EMBODIMENTS

Figure 1A:
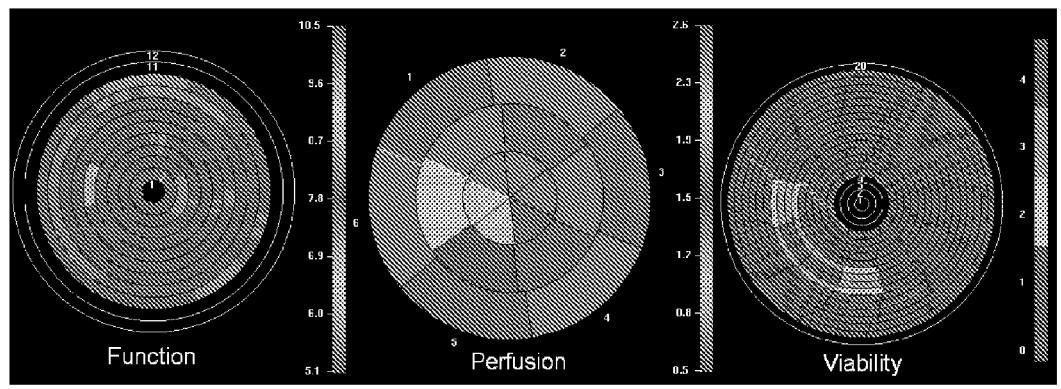
FIG. 1A shows exemplary prior art bull's eye plots for a function, perfusion and viability scan.
Figure 1B:
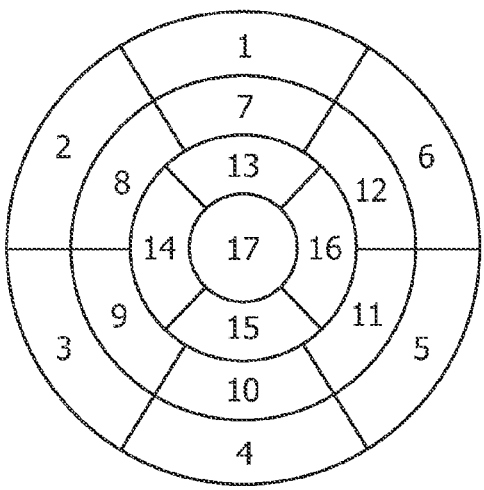
FIG. 1B schematically shows left ventricular bull's eye plot sectors and the corresponding myocardial slices and sectors according to the AHA model.
Figure 1B:
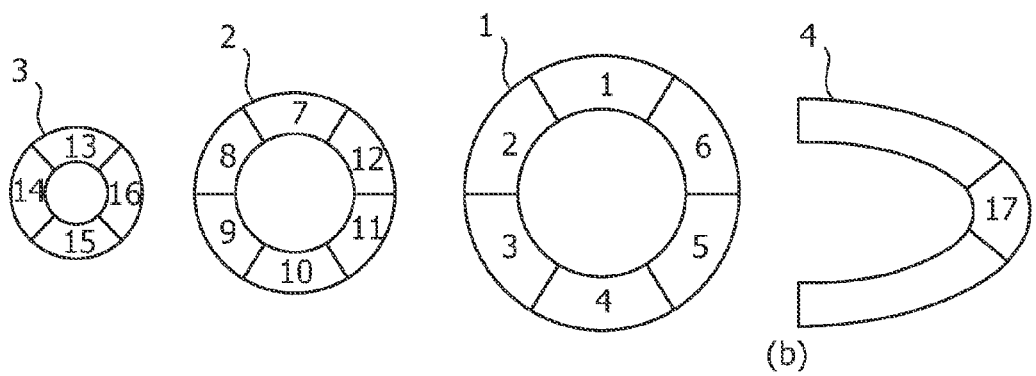
Figure 2:
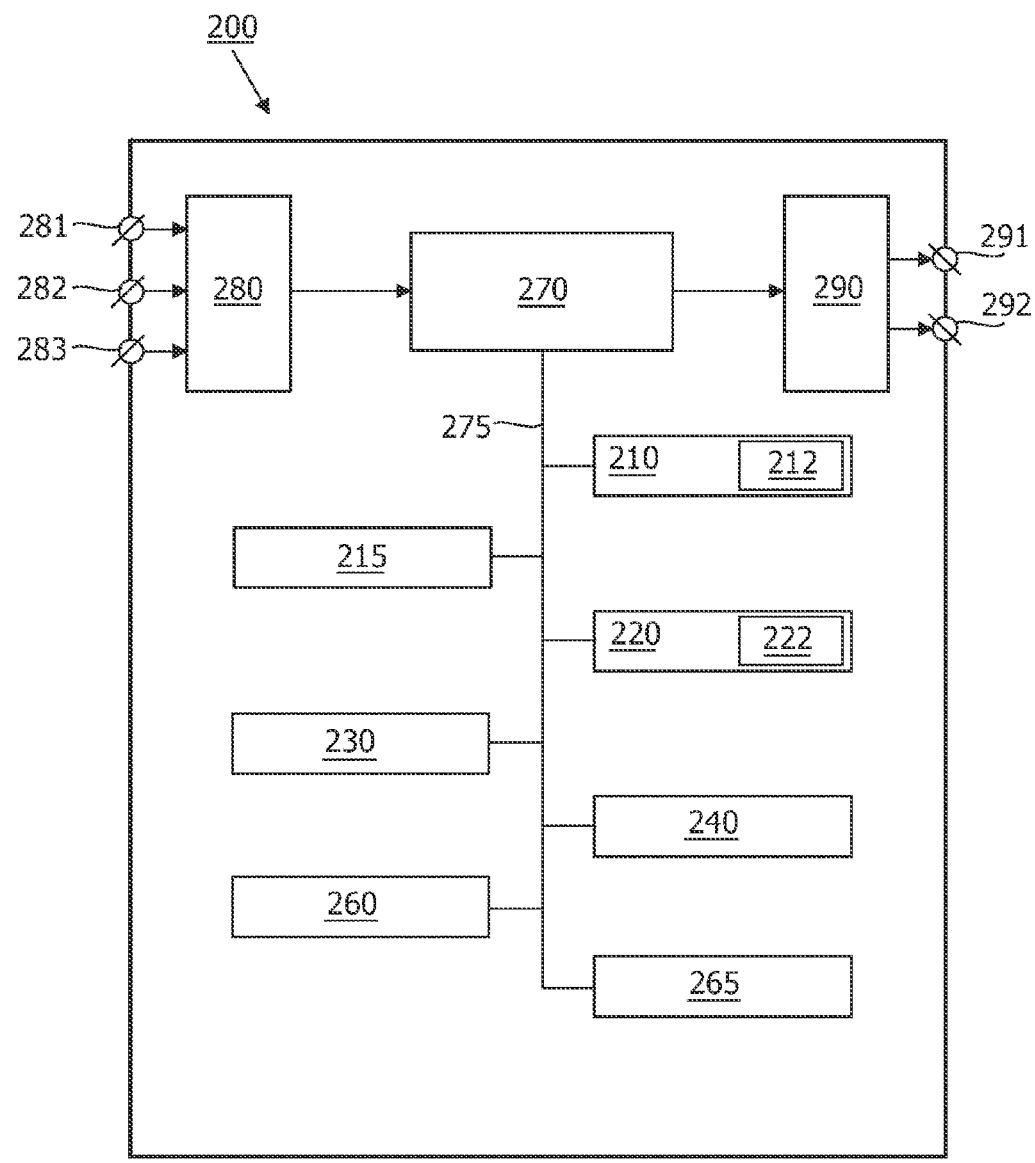
FIG. 2 schematically shows a block diagram of an exemplary embodiment of the system.

FIG. 2 schematically shows a block diagram of an exemplary embodiment of the system 200 for visualizing, in a first bull's eye plot, results of a first quantitative analysis of an object represented in first image data, the first image data comprising a first plurality of data slices, the system 200 comprising:

a slice unit 210 for associating a data slice of the first plurality of data slices with a concentric ring of the first bull's eye plot;

a radius unit 215 for computing the length of a radius of the concentric ring of the first bull's eye plot; and a value unit 220 for computing at least one value for displaying in the concentric ring of the first bull's eye plot, on the basis of the data slice associated with the concentric ring of the first bull's eye plot;

and wherein the length of a radius of the concentric ring of the first bull's eye plot is defined on the basis of the position of the data slice, of the first plurality of data slices, associated with the concentric ring of the first bull's eye plot, with respect to the object.

In the exemplary embodiment of the system 200, the slice unit 210 further comprises a slice-sector unit 212 for associating the data sector of the data slice with a ring sector of the concentric ring; and the value unit 220 comprises a sector-value unit 222 for computing at least one value for displaying in the ring sector of the concentric ring, on the basis of the data sector associated with the ring sector of the concentric ring;

and the position of the ring sector with respect to the concentric ring is defined on the basis of the position of the data sector associated with the ring sector, with respect to the object.

The exemplary embodiment of the system 200 further comprises the following units:

an approximation unit 230 for computing at least one value for displaying in a concentric ring gap of the first bull's eye plot on the basis of data slices of the first plurality of data slices associated with concentric rings adjacent to the ring gap;

a slice determination unit 240 for determining a first ring comprising the first location, based on a first data slice associated with the first ring and for determining a second ring comprising the second location, based on a second data slice associated with the second ring;

a control unit 260 for controlling the workflow in the system 200;

a user interface 265 for communicating with a user of the system 200; and a memory unit 270 for storing data.

In an embodiment of the system 200, there are three input connectors 281, 282 and 283 for the incoming data. The first input connector 281 is arranged to receive data coming in from a data storage means such as, but not limited to, a hard disk, a magnetic tape, a flash memory, or an optical disk. The second input connector 282 is arranged to receive data coming in from a user input device such as, but not limited to, a mouse or a touch screen. The third input connector 283 is arranged to receive data coming in from a user input device such as a keyboard. The input connectors 281, 282 and 283 are connected to an input control unit 280.

In an embodiment of the system 200, there are two output connectors 291 and 292 for the outgoing data. The first output connector 291 is arranged to output the data to a data storage means such as a hard disk, a magnetic tape, a flash memory, or an optical disk. The second output connector 292 is arranged to output the data to a display device. The output connectors 291 and 292 receive the respective data via an output control unit 290.

A person skilled in the art will understand that there are many ways to connect input devices to the input connectors 281, 282 and 283 and the output devices to the output connectors 291 and 292 of the system 200. These ways comprise, but are not limited to, a wired and a wireless connection, a digital network such as, but not limited to, a Local Area Network (LAN) and a Wide Area Network (WAN), the Internet, a digital telephone network, and an analog telephone network.

In an embodiment of the system 200, the system 200 comprises a memory unit 270. The system 200 is arranged to receive input data from external devices via any of the input connectors 281, 282, and 283 and to store the received input data in the memory unit 270. Loading the input data into the memory unit 270 allows quick access to relevant data portions by the units of the system 200. The input data may comprise, for example, the first image data. Optionally, the input data may further comprise a definition of data sectors, of the bull's eye plot ring sectors and of the correspondence between said bull's eye plot ring sectors and the structure sectors. The memory unit 270 may be implemented by devices such as, but not limited to, a Random Access Memory (RAM) chip, a Read Only Memory (ROM) chip, and/or a hard disk drive and a hard disk. The memory unit 270 may be further arranged to store the output data. The output data may comprise, for example, the computed first bull's eye plot data. The memory unit 270 may be also arranged to receive data from and/or deliver data to the units of the system 200 comprising the slice unit 210 further comprising the slice-sector unit 212, the radius unit 215, the value unit 220 further comprising the sector-value unit 222, the approximation unit 230, the slice determination unit 240, the control unit 260, and the user interface 265, via a memory bus 275. The memory unit 270 is further arranged to make the output data available to external devices via any of the output connectors 291 and 292. Storing data from the units of the system 200 in the memory unit 270 may advantageously improve performance of the units of the system 200 as well as the rate of transfer of the output data from the units of the system 200 to external devices.

Alternatively, the system 200 may comprise no memory unit 270 and no memory bus 275. The input data used by the system 200 may be supplied by at least one external device, such as an external memory or a processor, connected to the units of the system 200. Similarly, the output data produced by the system 200 may be supplied to at least one external device, such as an external memory or a processor, connected to the units of the system 200. The units of the system 200 may be arranged to receive the data from each other via internal connections or via a data bus.

In an embodiment of the system 200, the system 200 comprises a control unit 260 for controlling the workflow in the system 200. The control unit may be arranged to receive control data from and provide control data to the units of the system 200. For example, after associating a data slice with a concentric ring, the slice unit 210 may be arranged to provide control data "the data slice is associated with the concentric ring" to the control unit 260 and the control unit 260 may be arranged to provide control data "calculate the radius of the concentric ring" to the radius unit 215 and "calculate the values for displaying in the concentric ring" to the value unit 220. Alternatively, a control function may be implemented in another unit of the system 200.

In an embodiment of the system 200, the system 200 comprises a user interface 265 for communicating with the user of the system 200. The user interface may be arranged to display bull's eye plots. Further, the user interface 265 may be arranged to receive a user input for defining ring sectors and/or for indicating locations in the bull's eye plots. A person skilled in the art will understand that more functions may be advantageously implemented in the user interface 265 of the system 200.

The embodiments of the invention are described with reference to cardiac bull's eye plots, where the object is the left ventricle of the human heart. Those skilled in the art will understand, however, that the described application should not be construed as limiting the scope of the claims and that other applications are also conceivable.

In an embodiment of the system 200, the values computed by the value unit 220 are visualized using color coding. The center of the concentric rings of the bull's eye plot corresponds to the long axis of the left ventricle. The length of the external radius of each ring of the bull's eye plot is proportional to the distance from the apex of the left ventricle to the top planar surface of the data slice associated with the concentric ring by the slice unit 210.

In an embodiment of the system 200, the bull's eye plots are computed at high resolution and appear smooth in the sense that they do not show ring borders. This can be achieved in several ways. For example, the rings of the bull's eye plot may be thin and densely distributed on the plane of the bull's eye plot. This is possible if the image data set comprises a large number of substantially adjacent data slices. Each ring may be further divided into densely distributed small sectors. The widths of the rings and the sizes of the sectors are such that the human eye does not see borders between the sectors. For example, the sector size may be smaller than the size of a display pixel and thus the image granularity is determined by the display resolution. Alternatively or additionally, the approximation unit 230 may be employed for computing approximate values on the basis of the values computed in the rings or ring sectors of the bull's eye plot. Depending on the approximation method, the bull's eye plots may appear as low-resolution plots (e.g. when the number of rings and/or sectors is small, so that the rings or sectors scarcely cover the bull's eye plot and a step-function interpolation is employed) or as high-resolution smooth plots (e.g. when the third-degree polynomial interpolation is employed).

Figure 3:
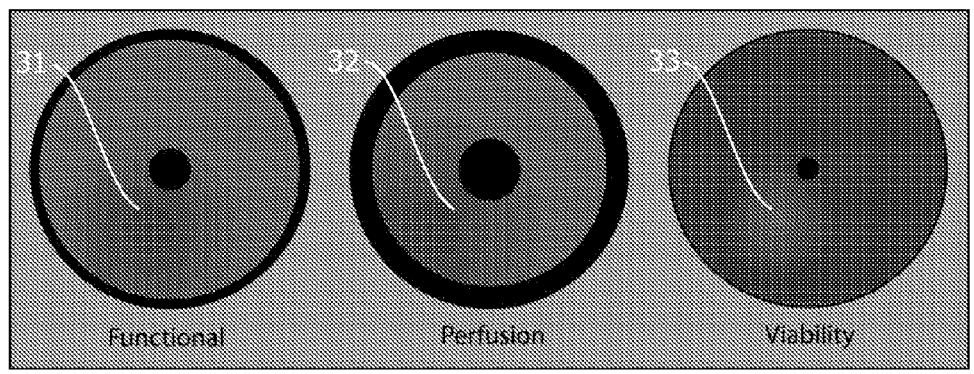
FIG. 3 shows exemplary bull's eye plots based on a function, perfusion and viability scan according to the invention.

FIG. 3 shows exemplary bull's eye plots according to the invention, obtained on the basis of a function (the left, first bull's eye plot), perfusion (the middle, second bull's eye plot) and viability (the right, third bull's eye plot) scan, using interpolation of missing bull's eye plot values. The plots appear to be smooth because the missing pixel values in the bull's eye plots are interpolated. Each location in the bull's eye plot relates to a particular location at the myocardium. Consequently, it becomes easier to relate findings from different scans. For example, from these bull's eye plots, it is immediately evident that the perfusion deficit 31 relates to a wall motion abnormality 32 and to a scar 33. It is worth pointing out that the range of different scans is also different. Thus, the blank areas in the bull's eye plots (visible as black areas of zero intensity and corresponding to the absence of image data) are different in each plot.

A person skilled in the art will understand that a number of various embodiments of the system 200 are possible. These embodiments may differ from each other, for example, with respect to the parameterization of the bull's eye plot. The radius of the bull's eye plot may be parameterized by the distance from the apex to the data slice or the distance from the valve plane to the data slice.

In an embodiment of the system 200, the length of the radius of each ring of the bull's eye plot is computed on the basis of the ratio of the distance from the apex to the data slice associated with the ring, to the distance between the apex and the valve plane.

Alternatively, the distance between other two landmarks of the heart and/or of the surrounding anatomy may be used to compute the ratio.

In an embodiment of the system 200, the radius unit is arranged for finding a position of at least one landmark in the image data. The skilled person will know various methods, e.g. segmentation methods, suitable for finding positions of such landmarks.

In an embodiment of the system 200, the length of the radius of each ring of the bull's eye plot is computed by the radius unit 215 on the basis of the thickness of data slices of the first plurality of data slices. For example, the length of the internal radius of the ring may be proportional to the sum of thicknesses of data slices of the plurality of data slices and, if the slices are not contiguous, of widths of inter-slice gaps, which data slices and inter-slice gaps are located between the data slice associated with the ring and a reference data slice. The length of the external radius of the ring may be equal to the sum of the thickness of the data slice associated with the ring and the internal ring radius. The reference data slice may be determined based on image data segmentation, for example, to comprise a reference landmark, e.g., the apex.

If two or more image data sets, each image data set comprising a plurality of data slices, are acquired in one exam such that the position of the patient with respect to the image acquisition apparatus is the same during each image data set acquisition, the radius of the ring of the bull's eye plot may be defined based on the position of the data slice associated with the ring in a laboratory system of reference. A laboratory system of reference is a system of reference defined with respect to the image acquisition apparatus. The z axis of the laboratory system is typically perpendicular to the data slices and substantially coincides with the long axis of the left ventricle of the myocardium. The radius of each ring of each bull's eye plot is computed based on the position of the data slice with respect to the z axis of the laboratory system. In this embodiment it is not necessary to determine landmark positions.

Furthermore, different embodiments may involve interpolation of different orders, i.e. linear, quadric, cubic, etc. Alternatively, the ring gaps corresponding to gaps between the data slices may remain blank in the bull's eye plot. The width of the ring may be related to the thickness of the data slice in the image stack comprising the plurality of data slices and the width of the ring gap may represent the width of the gap in the image stack of data slices associated with said ring gap.

In an embodiment, the system 200 further comprises an indicator input unit, implemented within the user interface 265, for receiving a user input for indicating a first location in the first bull's eye plot, using a first indicator, and a second location in the second bull's eye plot, using a second indicator, and an indicator unit, implemented within the user interface 265, for indicating the first location in the first bull's eye plot, using the first indicator, and the second location in the second bull's eye plot, using the second indicator, wherein the first and second locations are substantially the same relative to the respective first and second bull's eye plots. Thus, the first and second locations correspond to substantially identical locations in the first and second image data. This is possible because of the reparametrization of the bull's eye plot.

Figure 4:
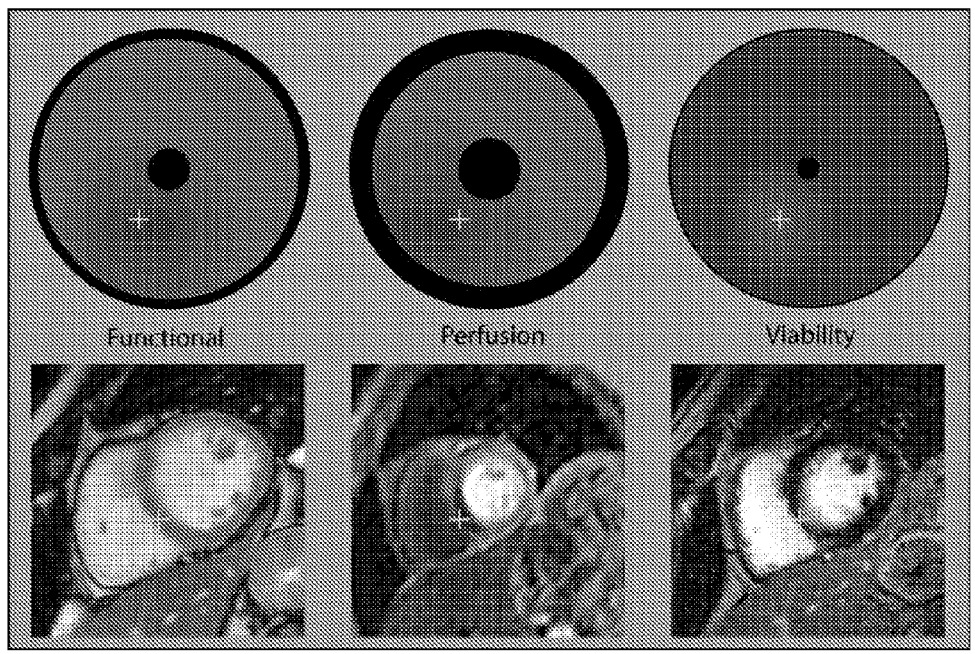
FIG. 4 shows exemplary bull's eye plots, each plot showing an indicated location, and exemplary images computed from data slices associated with rings comprising the indicated locations.

FIG. 4 shows exemplary bull's eye plots, each plot showing an indicated location, and exemplary images computed from data slices associated with rings comprising the indicated locations. Each location is indicated by a cross. The location of the cross in one of the bull's eye plots is determined by a pointer controlled by a mouse controlled by a user. The two other locations are computed based on said one location in such a way that all three locations are identical relative to the respective bull's eye plots. FIG. 4 illustrates an exemplary interactive comprehensive view based on cardiac MR data according to the invention. The mouse pointer (the cross) is used to indicate a scar in the bull's eye plot derived from the viability image. Linked pointers indicate the same location in the other bull's eye plots. A person skilled in the art will understand that, in principle, the linked pointers can be used to indicate corresponding locations in a plurality of bull's eye plots visualizing results of a plurality of analyses of a plurality of image data sets of an organ, even if the bull's eye plots are not reparametrized. In this case, each linked pointer may point at a different location in each bull's eye plot.

In addition, the system 200 may be further adapted for displaying images computed from data slices associated with bull's eye plot rings, comprising a location indicated by the pointer, as shown in FIG. 4. Each image computed from a data slice may further include a pointer for indicating a location corresponding to the location in the ring associated with the shown slice. Those skilled in the art will appreciate that the one-to-one correspondence between a location in a bull's eye plot and a location in the data slice associated with a ring comprising said location allows the input to be based either on a pointer location in the bull's eye plot or on a pointer location in a data slice. The user may inspect the stack of data slices, select a slice and indicate a location in a data slice which is of interest to him. The system (200) may be adapted for computing the corresponding location in the bull's eye plot. Additionally or alternatively, the ring associated with the selected slice may be shown in the bull's eye plot.

Figure 5:
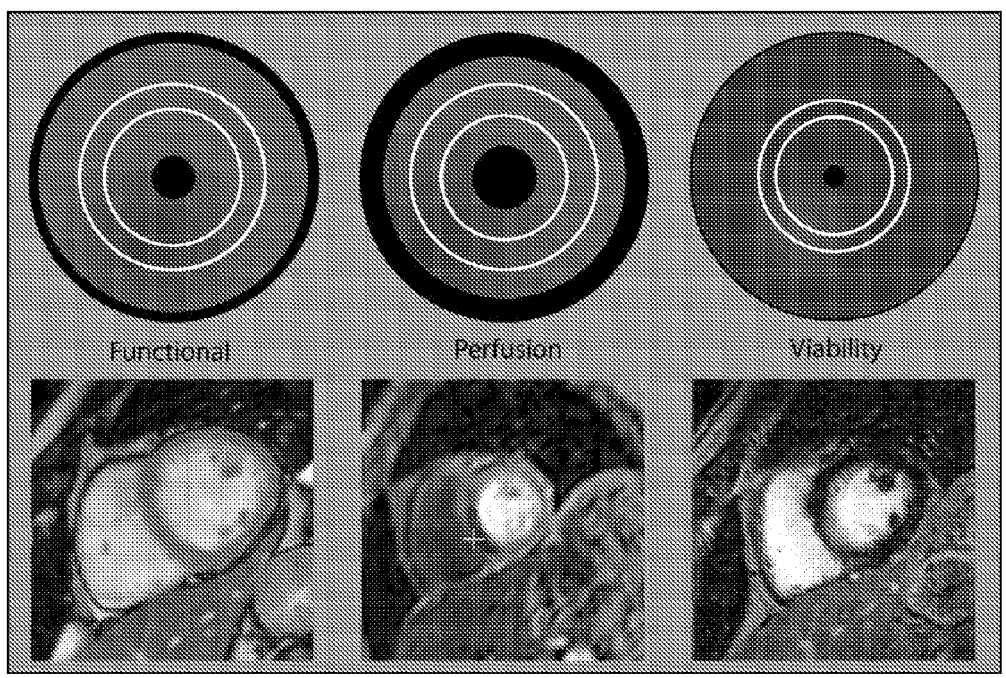
FIG. 5 shows exemplary bull's eye plots, each plot showing an indicated ring, and exemplary images computed from data slices associated with the indicated rings.
Figure 6:
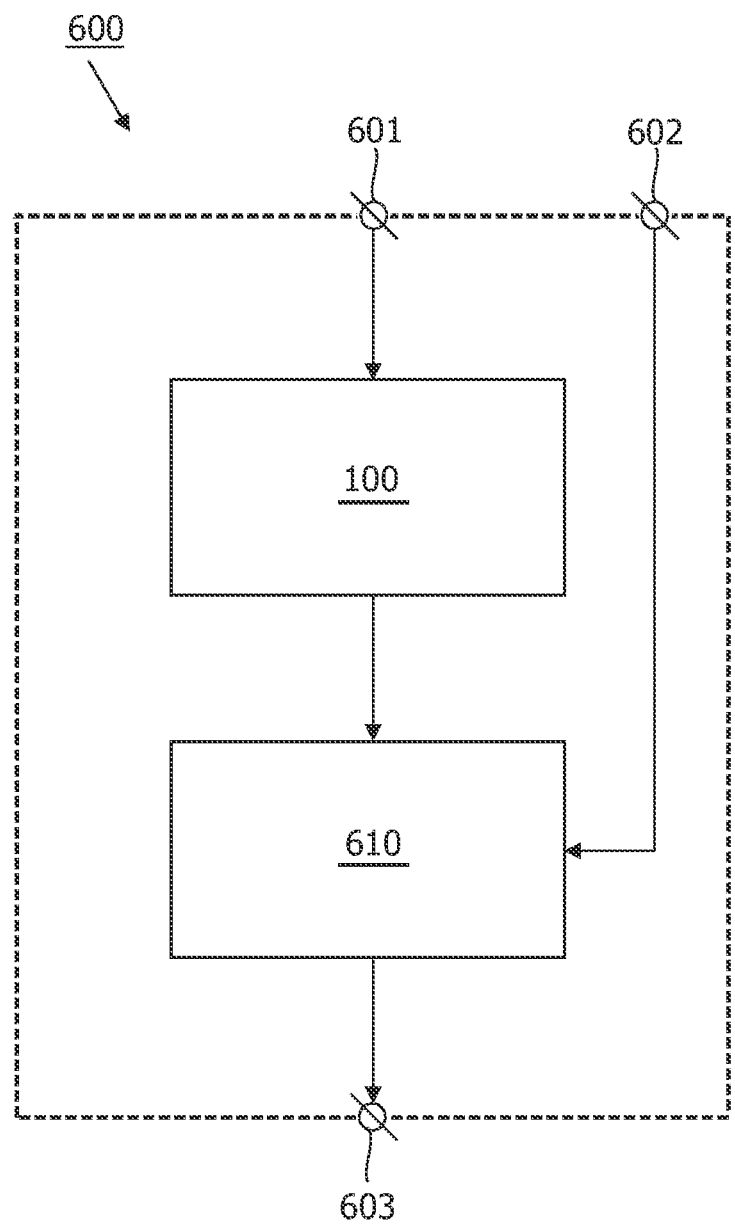
FIG. 6 schematically shows an exemplary embodiment of the reporting system.

FIG. 5 shows exemplary bull's eye plots, each plot showing an indicated ring, and exemplary images computed from data slices associated with the indicated rings. FIG. 5 illustrates an exemplary interactive comprehensive view based on cardiac MR data. The mouse pointer (the cross) is used to indicate a perfusion deficit in the perfusion image. In each bull's eye plot, the circles indicate the rings associated with the data slices corresponding to the location of the perfusion deficit.

The above embodiment of the system 200 implements a new method of interactive simultaneous visualization of the results from a comprehensive cardiac exam. The disclosed user interaction allows "result-driven" browsing through the acquired images by using the location of the mouse pointer in the bull's eye plots to display the slice related to that measurement. This interaction can be used in a linked fashion, such that a number of bull's eye plots can be used to select a slice of interest from a number of acquisitions. Thus, it is possible to construct an interactive viewing application that displays the acquired images and bull's eye plots from function, perfusion and viability simultaneously. Pointing at a perfusion deficit in a bull's eye plot highlights quantitative results in the other bull's eye plots and selects the slices corresponding to the location pointed at in all three scans, as shown in FIGS. 4 and 5. Additionally, the viewing application may indicate the selected slices in the bull's eye plots by means of rings, as shown in FIG. 5.

The proposed user interaction provides a powerful mechanism to quickly select images from diseased locations in the heart based on quantitative cardiac analysis results. Furthermore, the simultaneous display of bull's eye plots and images from function, perfusion and viability allows cardiologist to diagnose in a very direct and simple approach. Furthermore, using the system 200 it is easy to select key images, often from a total of more than 2000 images, to be included in the final report.

In an embodiment, the system 200 is adapted for enabling the user, e.g. a cardiologist, to interactively delineate the myocardial contours in the examined image data. By displaying delineated contours and the acquired images, the cardiologist can quickly assess whether the delineation has been performed correctly, especially for a location with interesting measurement values.

Advantageously, the system 200 may be comprised in a reporting system 600. Thus, the system 200 may be included in a medical report created by a report unit 610 together with annotations by a physician examining the bull's eye plot. In an embodiment, the reporting system 600 comprises a reporting system first input connector 601 for obtaining data needed by the system 200 and a reporting system second input connector 602 for obtaining other data such as user annotations, patient name and age, other test and examination results, comments by a physician preparing the report, and so on. The reporting unit 610 is arranged to receive the bull's eye plots from the system 200. The report is outputted via a reporting system output connector 603.

Those skilled in the art will further understand that other embodiments of the system 200 are also possible. It is possible, among other things, to redefine the units of the system and to redistribute their functions. Although the described embodiments apply to medical images, other applications of the system, not related to medical applications, are also possible.

The units of the system 200 may be implemented using a processor. Normally, their functions are performed under the control of a software program product. During execution, the software program product is normally loaded into a memory, like a RAM, and executed from there. The program may be loaded from a background memory, such as a ROM, hard disk, or magnetic and/or optical storage, or may be loaded via a network like the Internet. Optionally, an application-specific integrated circuit may provide the described functionality.

Figure 7:
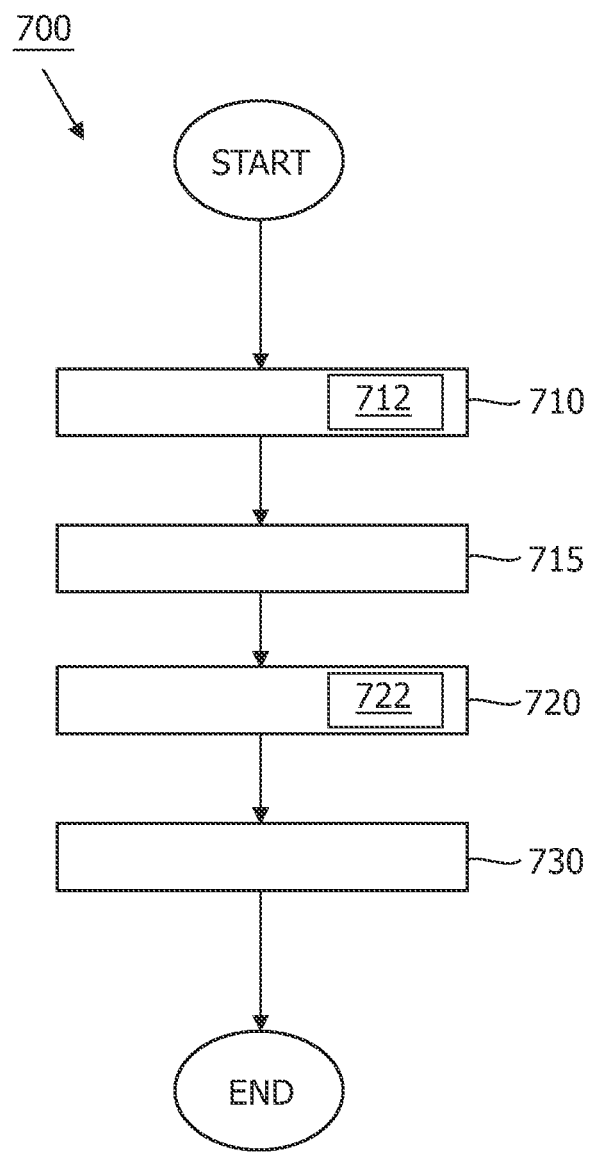
FIG. 7 shows a flowchart of an exemplary implementation of the method.

FIG. 7 shows a flowchart of an exemplary implementation of the method 700 of visualizing, in a first bull's eye plot, results of a first quantitative analysis of an object represented in first image data, the first image data comprising a first plurality of data slices. The method 700 begins with a slice step 710 for associating a data slice of the first plurality of data slices with a concentric ring of the first bull's eye plot. Optionally, the slice step may further involve a plurality of slice-sector steps 712 for associating the data sector of the data slice with a ring sector of the concentric ring. After the slice step 710, the method 700 continues to a radius step 715 for computing the length of a radius of the concentric ring of the first bull's eye plot. After the radius step 715, the method 700 continues to a value step 720 for computing at least one value for displaying in the concentric ring of the first bull's eye plot, on the basis of the data slice associated with the concentric ring of the first bull's eye plot. Optionally, the value step 220 may comprise a plurality of sector-value steps 722 for computing at least one value for displaying in the ring sector of the concentric ring, on the basis of the data sector associated with the ring sector of the concentric ring, and wherein the position of the ring sector with respect to the concentric ring is defined on the basis of the position of the data sector associated with the ring sector, with respect to the object. Optionally, after the value step 720, the method 700 continues to an approximation step 730 for computing at least one value for displaying in a concentric ring gap of the first bull's eye plot on the basis of data slices of the first plurality of data slices associated with concentric rings adjacent to the ring gap. After the value step 720 or after the approximation step 730, the method 700 terminates. In the method 700 according to the invention, the length of the radius of the concentric ring of the first bull's eye plot is defined on the basis of the position of the data slice, of the first plurality of data slices, associated with the concentric ring of the first bull's eye plot, with respect to the object.

A person skilled in the art may change the order of some steps or perform some steps concurrently using threading models, multi-processor systems or multiple processes without departing from the concept as intended by the present invention. For example, the radius step 215 and the value step 220 may be computed concurrently. Optionally, two or more steps of the method of the current invention may be combined into one step. Optionally, a step of the method of the current invention may be split into a plurality of steps.

Figure 8:
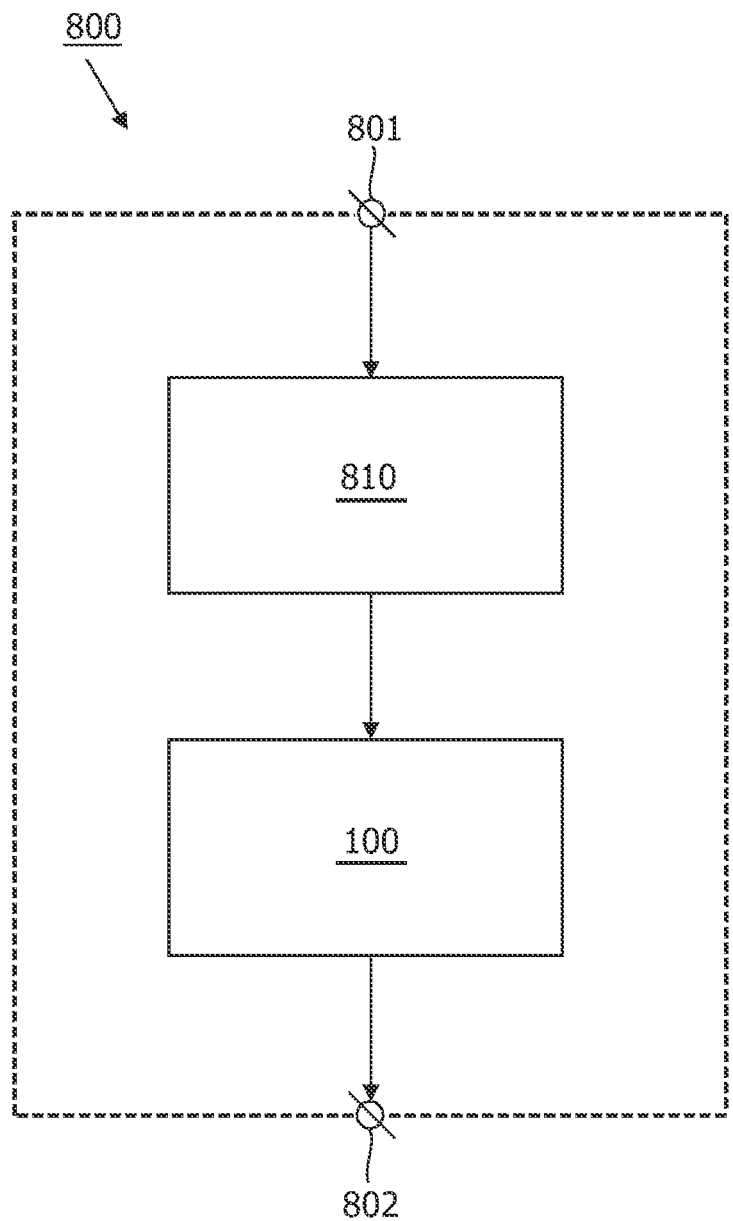
FIG. 8 schematically shows an exemplary embodiment of the image acquisition apparatus.

FIG. 8 schematically shows an exemplary embodiment of the image acquisition apparatus 800 employing the system 200, said image acquisition apparatus 800 comprising a CT image acquisition unit 810 connected via an internal connection with the system 200, an input connector 801, and an output connector 802. This arrangement advantageously increases the capabilities of the image acquisition apparatus 800, providing said image acquisition apparatus 800 with advantageous capabilities of the system 200.

Figure 9:
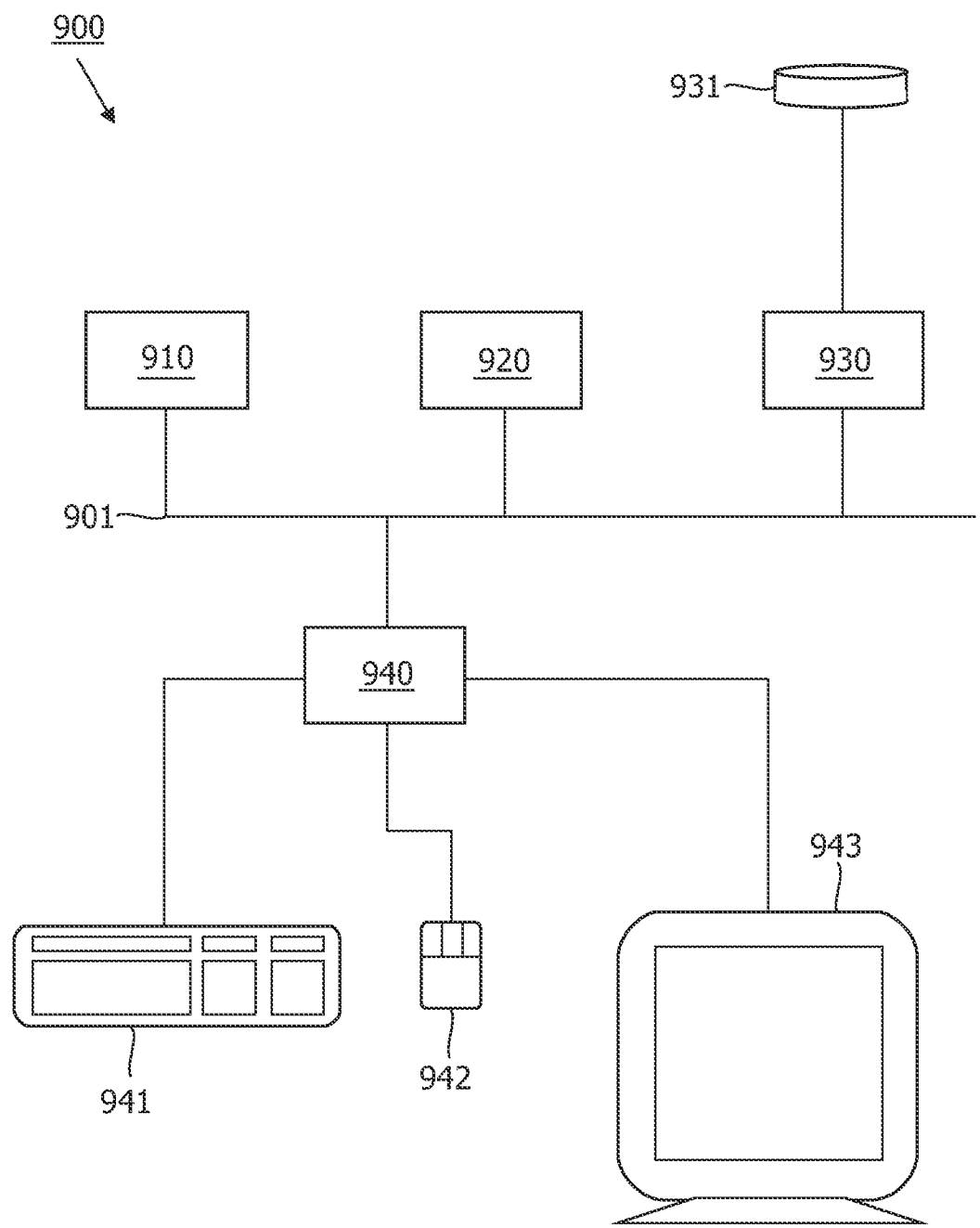
FIG. 9 schematically shows an exemplary embodiment of the workstation.

FIG. 9 schematically shows an exemplary embodiment of the workstation 900. The workstation comprises a system bus 901. A processor 910, a memory 920, a disk input/output (I/O) adapter 930, and a user interface (UI) 940 are operatively connected to the system bus 901. A disk storage device 931 is operatively coupled to the disk I/O adapter 930. A keyboard 941, a mouse 942, and a display 943 are operatively coupled to the UI 940. The system 200 of the invention, implemented as a computer program, is stored in the disk storage device 931. The workstation 900 is arranged to load the program and input data into memory 920 and execute the program on the processor 910. The user can input information to the workstation 900, using the keyboard 941 and/or the mouse 942. The workstation is arranged to output information to the display device 943 and/or to the disk 931. A person skilled in the art will understand that there are numerous other embodiments of the workstation 900 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second, third, etc., does not indicate any ordering. These words are to be interpreted as names.

The invention claimed is:

1. A system for concurrently displaying, in first and second bull's eye plots, results of a first and second quantitative analysis of an object represented in first and second image data, the first and second image data comprising a first and second plurality of data slices, respectively; the system comprising:
   a slice unit that associates a data slice of the first plurality of data slices with a concentric ring of the first bull's eye plot;
   a radius unit that computes the length of a radius of the concentric ring of the first bull's eye plot; and
   a value unit that computes at least one value for displaying in the concentric ring of the first bull's eye plot, on the basis of the data slice associated with the concentric ring of the first bull's eye plot;
   wherein the length of the radius of the concentric ring of the first bull's eye plot is defined on the basis of the position of the data slice of the first plurality of data slices associated with the concentric ring of the first bull's eye plot with respect to the object;
   the system being further adapted to concurrently display, in the second bull's eye plot, the results of the second quantitative analysis of the object represented in the second image data, wherein:
   the slice unit associates a data slice of the second plurality of data slices with a concentric ring of the second bull's eye plot;
   the radius unit computes the length of a radius of the concentric ring of the second bull's eye plot; and
   the value unit computes at least one value for displaying in the concentric ring of the second bull's eye plot on the basis of the data slice associated with the concentric ring of the second bull's eye plot;
   wherein the length of the radius of the concentric ring of the second bull's eye plot is defined on the basis of the position of the data slice of the second plurality of data slices associated with the concentric ring of the second bull's eye plot with respect to the object; and
   wherein the system further includes:
   an indicator input unit that receives a user input for indicating a first location in the first bull's eye plot, and
   an indicator unit that indicates the first location in the first bull's eye plot, and determines and indicates a second location in the second bull's eye plot corresponding to the first location in the first bull's eye plot.

2. A system as claimed in claim 1, wherein the data slice associated with the concentric ring comprises a data sector, wherein the slice unit further comprises a slice-sector unit that associates the data sector of the data slice with a ring sector of the concentric ring, wherein the value unit comprises a sector-value unit that computes at least one value for displaying in the ring sector of the concentric ring, on the basis of the data sector associated with the ring sector of the concentric ring, and wherein the position of the ring sector with respect to the concentric ring is defined on the basis of the position of the data sector associated with the ring sector, with respect to the object.

3. A system as claimed in claim 1, wherein the first bull's eye plot comprises a concentric ring gap corresponding to an inter-slice gap.

4. A system as claimed in claim 3, further comprising an approximation unit that computes at least one value for displaying in the concentric ring gap of the first bull's eye plot on the basis of data slices of the first plurality of data slices associated with concentric rings adjacent to the ring gap.

5. A system as claimed in claim 4, wherein the at least one value for displaying in the concentric ring gap of the first bull's eye plot is computed on the basis of values for displaying in the concentric rings adjacent to the ring gap, which values are computed on the basis of data slices of the first plurality of data slices, associated with the concentric rings adjacent to the gap.

6. A system as claimed in claim 1, wherein the length of the radius of the concentric ring of the first bull's eye plot is computed on the basis of a distance between the data slice of the first plurality of data slices, associated with the concentric ring, and a certain feature of the object.

7. A system as claimed in claim 6, wherein the width of the concentric ring of the first bull's eye plot is computed on the basis of the thickness of the data slice of the first plurality of data slices.

8. A system as claimed in claim 1, wherein the lengths of the radiuses of the concentric ring of the first bull's eye plot and of the concentric ring of the second bull's eye plot are computed on the basis of distances from, respectively, the data slice of the first plurality of data slices and the data slice of the second plurality of data slices to a certain feature of the object.

9. A system as claimed in claim 1, further comprising a slice determination unit that determines a first ring comprising the first location, based on a first data slice associated with the first ring and a second ring comprising the second location, based on a second data slice associated with the second ring.

10. A system as claimed in claim 9, wherein the user input for indicating the first location in the first bull's eye plot comprises indicating a certain location in a certain data slice of the first plurality of data slices.

11. An image acquisition apparatus comprising the system as claimed in claim 1.

12. A workstation comprising the system as claimed in claim 1.

13. A non-transitory computer readable medium that includes a computer program that, when executed by a processor, causes the processor to:
   receive a first plurality of data slices and a second plurality of data slices corresponding to an object;

for each first data slice of the first plurality of data slices:
    determine a radius of a concentric ring of a first bull's eye plot that is based upon a distance of the first data slice from a feature of the object,
    determine a first set of values for display in the concentric ring of the first bull's eye plot;
for each second data slice of the second plurality of data slices:
    determine a radius of a concentric ring of a second bull's eye plot that is based upon a distance of the second data slice from the feature of the object,
    determine a second set of values for display in the concentric ring of the second bull's eye plot;
display the determined values in the concentric rings of the first bull's eye plot;
concurrently display the determined values in the concentric rings of the second bull's eye plot;
receive a user input that identifies a first point at a location in the first bull's eye plot;
determine a second point in the second bull's eye plot corresponding to the location in the first bull's eye plot; and
concurrently display an indication of the first point in the first bull's eye plot and the second point in the second bull's eye plot.

14. The medium of claim 13, wherein the computer program causes the processor to:
determine a select data slice of the first plurality of data slices corresponding to the first point;
display an image corresponding to the select data slice;
determine a location of a point in the image corresponding to the first point; and
display an indication of the point in the image.

15. The medium of claim 13, wherein the image is concurrently displayed with the first and second bull's eye plots.

16. The medium of claim 13, wherein the computer program causes the processor to:
display an image corresponding to a select data slice of the first plurality of data slices;
receive a user input that identifies a select point in the image;
determine a first point in the first bull's eye plot and a second point in the second bull's eye plot, each corresponding to the select point in the image; and
displaying an indication of the first point in the first bull's eye plot and the second point in the second bull's eye plot.

17. The medium of claim 16, wherein displaying an indication of the first point in the first bull's eye plot includes displaying an indication of the concentric ring containing the first point in the first bull's eye plot.

18. A method comprising:
creating, on a processing system, a first bull's eye plot based on a first plurality of data slices corresponding to image data of an object that is stored in a computer-readable memory,
creating, on the processing system, a second bull's eye plot based on a second plurality of data slices corresponding to second image data of the object,
concurrently displaying the first and second bull's eye plots on a display device,
wherein for each bull's eye plot, values determined corresponding to each data slice are displayed in a concentric ring, the radius of the concentric ring being determined by a distance of the data slice from a feature on the object;
the method further including:
receiving a user input that identifies a first point at a location in the first bull's eye plot,
determining a second point in the second bull's eye plot corresponding to the location in the first bull's eye plot, and
concurrently displaying an indication of the first point in the first bull's eye plot and the second point in the second bull's eye plot.

* * * * *